United States Patent [19]

Ueno et al.

[11] Patent Number: 4,918,202

[45] Date of Patent: Apr. 17, 1990

[54] PRECURSOR OF PROSTAGLANDIN

[75] Inventors: Ryuzo Ueno; Ryuji Ueno, both of Nishinomiya; Tomio Oda, Sanda, all of Japan

[73] Assignee: Kabushiki Kaisha Ueno Seiyaku Oyo Kenkyujo, Osaka, Japan

[21] Appl. No.: 386,074

[22] Filed: Jul. 28, 1989

[30] Foreign Application Priority Data

Jul. 29, 1988 [JP] Japan ................... 63-191190

[51] Int. Cl.$^4$ ............................................. C07D 493/04
[52] U.S. Cl. .................................................. 549/299
[58] Field of Search ........................................ 549/299

[56] References Cited

U.S. PATENT DOCUMENTS 4,115,404 9/1978 Greenhough et al. ...... 260/343.3 R
4,204,999 5/1980 Tömösközi et al. ............ 260/340.3

*Primary Examiner*—Richard A. Schwartz
*Assistant Examiner*—Richard A. Sharpe
*Attorney, Agent, or Firm*—Sughrue, Mion, Zinn, Macpeak & Seas

[57] ABSTRACT

The present invention provides new compound, 10-substituted-5,9-dioxatricyclo[6.4.0.0$^{2,6}$]dodecane-4-one, which is very useful as an intermediate for prostaglandin synthesis.

5 Claims, No Drawings

PRECURSOR OF PROSTAGLANDIN

BACKGROUND OF THE INVENTION

The present invention relates to a precursor of prostaglandins, 10-substituted-5,9-dioxatricyclo-[6.4.0.0.$^{2,6}$]dodecane-4-one, which is a new compound and useful as an intermediate for production of prostaglandins, and process for production thereof.

Prostaglandins (referred to as PGs hereinafter) are a general name of a compound having a basic skeleton represented by the formula:

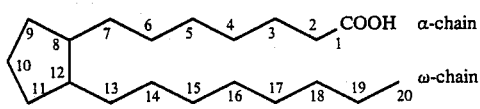

which are found in, for instance, tissues, organs, metabolites of humans and animals. PGs have lately attracted considerable attention as various kinds of medicament because of their great variety of physiological activities. Recently, it has been tried to develop new PGs and their derivatives exhibiting a specific activity to a pathological condition to be controlled with less or without side effects. We have studied synthesis and pharmacological activities of PGs in which the 13- and 14-position are saturated and the carbon atom of the 15-position forms carbonyl group, that is, 13,14-dihydro-15-keto-PGs, and found that they exhibit specific activity in comparison with natural PGs (Japanese Patent Application Nos. 18326/1988, 108329/1988 etc.).

According to a typical and conventional process for producing PG derivatives, at least three processes are indispensably applied to introduce a protective group for the carbonyl group in the ω-chain before the α-chain is introduced into the compound (4) derived from Corey lactone as shown in the synthetic chart.

SUMMARY OF THE INVENTION

The present invention provides a simple method of reducing the number of processes for protecting the carboxyl group in the ω-chain and hydroxyl groups on the five membered ring in the production of 13,14-dihydro-15-keto-PGs with high yield.

Further, the present invention provides new compounds obtained as intermediates in the above method, that is, 10-substituted-5,9-dioxatricyclo[6.4.0.0$^{2,6}$]-dodecane-4-one.

DETAILED DESCRIPTION OF THE INVENTION

The present invention relates to new compounds 10-substitued-5,9-dioxatricyclo[6.4.0.0$^{2,6}$]dodecane-4-one useful as intermediates for production of 13,14-dihydro-15-keto-PGs, which are represented by the formula [II]:

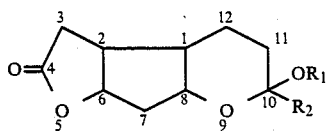

wherein $R_1$ is a hydrocarbon group, $R_2$ is a saturated or unsaturated hydrocarbon group which may have one or more substituent(s), and production thereof.

The compound, 10-substituted-5,9-dioxatricyclo[6.4.0.0$^{2,6}$]dodecane-4-one can be prepared by the reaction of a compound having 3'-oxoalkyl group at 6-position, i.e. 7-hydroxy-2-oxabicyclo[3.3.0]octane-3-on represented by the formula [I]:

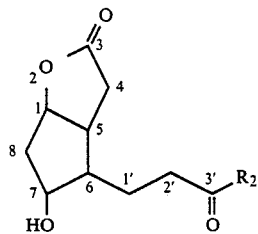

wherein $R_2$ is the same as the above with a hydroxyl compound $R_1OH$ wherein $R_1$ is the same as the above in the presence of an acidic catalyst to case a ring formation between the hydroxyl group at 7-position and the carbonyl group at 3'-position.

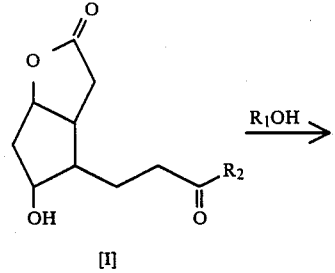

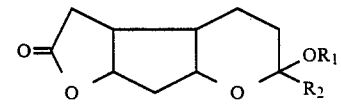

A compound [I], a raw material, itself is well known, which may be prepared from a commercially available Corey lactone according to a conventional method. One typical method of preparing the compound [I] is to subject Corey lactone (1) to Collins oxidation to give aldehyde (2), react the obtained aldehyde with a phosphonate having a 2-oxo(substituted)hydrocarbon group such as a dimethyl(2-oxoalkyl)phosphonate, and reduce the obtained α,β-unsaturated ketone, then eliminate p-phenylbenzoate.

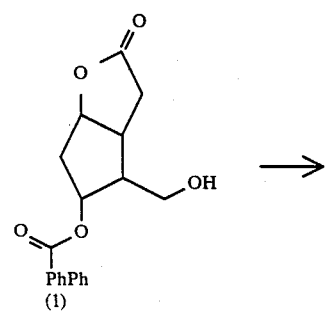

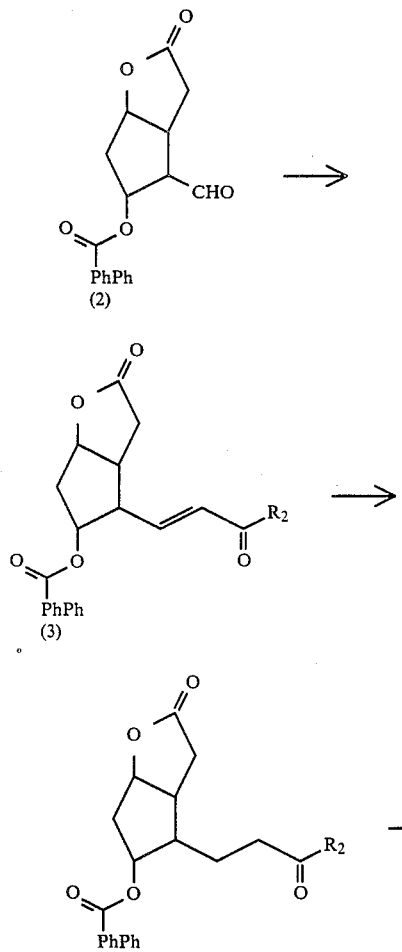

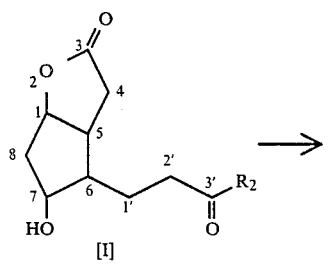

The compound [II] in which the carbonyl group and the hydroxyl group are protected can be obtained by cyclization between the carbonyl group at 3'-position and the hydroxyl group at 7-position as aforementioned.

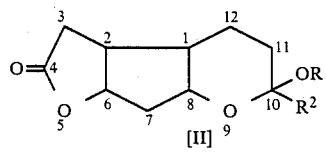

13,14-Dihydro-15-keto-PGs can be prepared by introducing a desired α-chain into the compound [II], transferring a necessary functional group, and finally hydrolysis the ring.

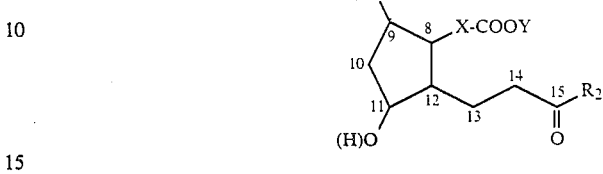

In the above reaction, $R_1OH$ may be a lower alcohol such as $C_{1-9}$ alcohols which may have one or more substituent(s) particularly methyl alcohol, ethyl alcohol, isopropyl alcohol, t-butyl alcohol; alicyclic alcohol such as cyclohexanol; or an alcohol having an aromatic group such as phenols, benzyl alcohols and the like, preferably lower alcohol such as methyl alcohol and ethyl alcohol, because it is used to only protect the carbonyl group and hydroxyl group by changing the compound (I) to a stable ring compound (II). $R_1OH$ may be used in much excess amount to the compound (I), which amount is not restricted, but is preferably from 2 to 100 ml to 1 g of the compound (I) in industrial, practical and economical aspects.

The acidic catalysts may include a mineral acid such as sulfuric acid; a organic acid such as alkyl sulfonic acid, benzene sulfonic acid, carboxylic acid such as oxalic acid; a quaternary ammonium salt such as pyridine hydrogen chloride; a Lewis acid such as boron trifluoride etherate; an acidic ion-exchange resin such as Amberist, and the like, which may be selected from acidic catalyst usually used for ketalation. Most preferable catalysts are alkyl sulfonic acid such as methyl sulfonic acid, camphor sulfonic acid and the like, aryl sulfonic acid such as p-toluene sulfonic acid, quaternary ammonium salts such as pyridinium p-toluenesulfonate, and acidic ion-exchange resin such as Amberist 15 and the like.

The acidic catalyst may be used in the amount of from 0.001 to 100 mole %, more preferably 0.01 to 50 mole %, based on the compound [I].

Reaction medium may include irrestrictively $R_1OH$ itself, saturated or unsaturated hydrocarbons such as hexane, aromatic hydrocarbons such as benzene, alkyl halides such as dichloromethane, nitriles such as acetonitrile, and ethers such as tetrahydrofuran and the like. The reaction may be carried out preferably between room temperature and refluxing temperature of $R_1OH$ used under a normal pressure or higher pressure. The reaction may be proceeded as removing water generating during the reaction if desired. The reaction time is usually about 1-48 hours.

$R_2$ of the compound [I] may be any hydrocarbons corresponding to the ω-chain of objective PGs, which may be saturated or unsaturated or have one or more substituents. Though the number of ω-chain of ordinary PGs is eight (i.e. the number of carbon atoms in $R_2$ is 5), it is not restricted in the present invention, and it may be one more, preferably 1-9. $R_2$ may be aliphatic hydrocarbons, alicyclic hydrocarbons such as a cyclohexyl group aromatic hydrocarbons such as a phenyl group, a benzyl group and the like, which may have one or more branch(es), unsaturated bond(s), and/or one or more substituent(s) at any position(s). Preferable groups of $R_2$ have one or more substituent(s) such as halogen atom(s), hydroxyl group(s), lower alkyl group(s) such as methyl group(s) at 4'-position when $R_2$ is an aliphatic group, and the carbon atoms of $R_2$ are numbered by 4', 5', 6', ... in this order starting from the carbon atom adjacent to the carbon atom numbered by 3' in the formula [I] (the carbon atoms numbered by 4', 5', 6', ... correspond to carbon atoms at the 16-, 17-, 18-, ... positions in an ordinary PGs); alkoxy groups or phenoxy groups which may have one or more substituent(s) at 4'-position; alkyl groups such as a methyl group and the like at 7'-position (19-position of PGs); and/or alkoxy groups such as a methoxy group, an ethoxy group and the like at 8'-position (20-position of PGs). Preferable compounds [II] in the present invention are those in which the group $R_2$ has six or more than six carbon atoms and the aforementioned substituent(s) in the aspect of PGs derived from such compounds [II]. Preferable examples of $R_2$ are pentyl, hexyl, heptyl, octyl, 1-chloropentyl, 1-fluoropentyl, 1,1-difluoropentyl, 1-fluorohexyl, 1-hydrosypentyl, 1-hydroxyhexyl, 1-methylpentyl, 1-methylhexyl, 1-methylheptyl, 1,1dimethylpentyl, 4-methylpentyl, 5-methylhexyl, 5-methylheptyl, m-trifluoromethylphenoxymetjhyl and the like.

The compounds [II] which are obtained by reacting the compounds [I] with $R_1OH$ may contain isomers corresponding to steric configuration of the Corey lactone (1), and isomers produced at the ring formation.

The compounds [I] derived from (−)Corey lactones by a conventional method are represented by the formula [I']. Compounds represented by the formula [II'] can be obtained by the ring formation of the compounds [I'] with $R_1OH$ in the presence of an acidic catalyst.

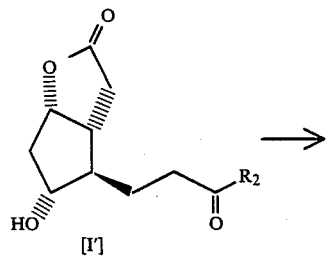
[I']

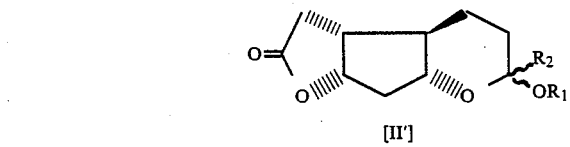
[II']

The compounds [II'] include any possible isomers.

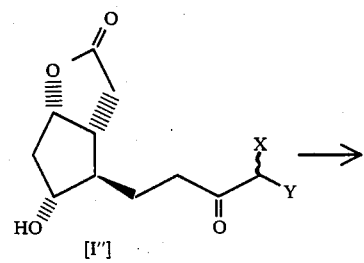
[I'']

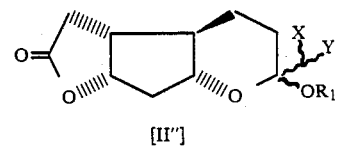
[II'']

The compound [II'] derived from the compound [I''] of which $R_2$ is, for example, 1-fluoroalkyl by the ring formation can be separated to two isomers, that is, an isomer having a larger polarity and the other having a smasller polarity on a thin layer chromatography.

13,14-Dihydro-15-keto-PGs can be produced by introducing α-chain into the compound [II] of the present invention, and then finally hydrolysis the ring of the obtained compound.

Whichever isomer of [II'] or [II''] is used as a compound [II], the PGs obtained contains no isomers. Therefore, both isomers of [II'] or those of [II''] are useful as intermediates for PGs.

Typical processes for preparing 13,14-dihydro-15-keto-PGs from the compound [II] are irrespectively illustrated hereinafter.

13,14-dihydro-15-keto-PGE$_2$ (12):

The compound [II] is reduced by DIBAL-H at the carbonyl group of the 4-position to give a lactol (10), into which α-chain is introduced by the reaction with, for instance, (4-carboxybutyl)triphenylphosphonium bromide to give compound (11). The compound (11) is esterified, subjected to Collins oxidation at the hydroxyl group of the 9-position (referred to the position number of carbon atom of ordinary PGs), and then hydrolyzed to open the ring.

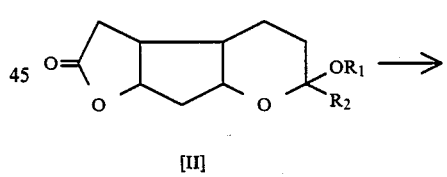
[II]

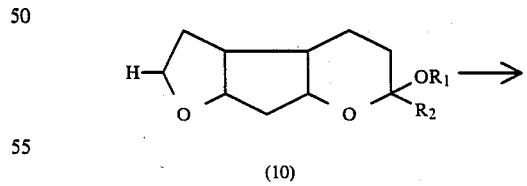
(10)

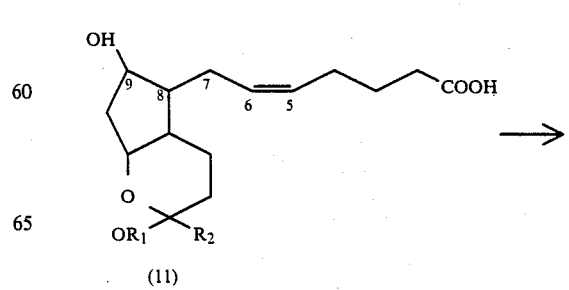
(11)

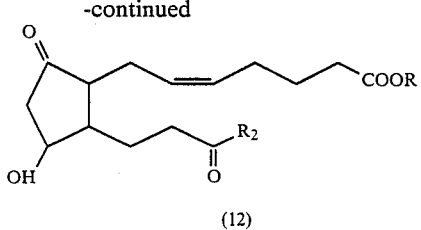

(12)

13,14-l-dihydro-15-keto-PGE$_1$s:

These compounds can be obtained by reducing the compound (11) at the double bond of α-chain using palladium catalysts or as such under hydrogen atmosphere, and then treating the reduced material in a similar manner to PGE$_2$

13,14-dihydro-6,15-diketo-PGE$_1$s:

The carboxyl group of the compound (11) is esterified, and the resultant is cyclized between the double bond of α-chain and hydroxyl group of the 9-position using N-bromosuccinic imido or iodine to give a halogenized compound. Dehydrohalogenation of the resultant using DBU yields a 6-keto intermediate which is subjected to Collins oxidation at a hydroxyl group of the 9-position, and then hydrolyzed to open the ring.

13,14-dihydro-15-keto-PGF$_2$s:

These compounds can be obtained by the hydrolysis of ring of the compound (11) after the protection of the carboxyl group.

13,14-dihydro-15-keto-PGF$_1$s:

These compounds can be obtained by the reduction of double bond of the α-chain after the protection of the carboxyl group of the compound (11), and the successive hydrolysis of the ring.

13,14-dihydro-6,15-diketo-PGF$_1$s:

6-Keto intermediates obtained in the production of 13,14-dihydro-6,15-diketo-PGE$_1$s as aforementioned are hydrolyzed without Collins oxidation to open the ring.

The present invention shall be illustrated by the following Examples, in which the compounds are nominated according to IUPAC.

EXAMPLE 1

(1) Synthesis of (1R,2R,6S,8R,10RS,10SR)-10-[1(RS)-fluoropentyl]-10-methoxy-5,9-dioxatricyclo-[6.4.0.0$^{2,6}$]dodecane-4-one:

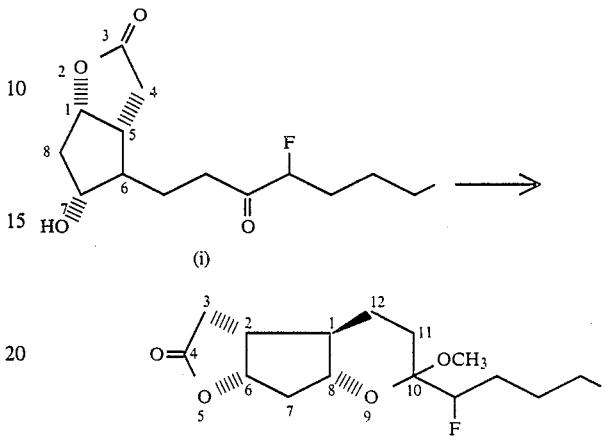

(1S,5R,6R,7R)-6-[4(RS)-fruolo-3-oxo-1-octyl]-7-hydroxy-2-oxabicyclo[3.3.0]octane-3-one (2.08 g) was dissolved in methanol, into which a catalytic amount of p-toluene sulfonic acid monohydrate was added, and the mixture heated under reflux for 48 hours. Into the reaction mixture a saturated aqueous solution of sodium bicarbonate was added, and subjected to a usual workup. A crude product obtained was subjected to column chromatography (hexane: ethyl acetate=1:1) to give a diastereoisomer of the title compound (yield: 1.47 g, 62.8%).

The NMR spectrum of the obtained compound is:
δ: 0.67–1.05 (3H, m), 1.07–2.98 (16H, m), 3.18 (1.5H, s), 3.25 (1.5H, s), 3.01–3.77 (1H, m), 400–4.25(0.5H, m), 4.55–5.05(1.5H, m)

(2) Synthesis of (1R,3RS,3SR,6R,7R,8S)-7-[6-carbomethoxy-(z)-2-hexenyl]-3-[1(RS)-fluoropentyl]-3-methoxy-2-oxabicyclo[4.3.0]nonane-8-ol:

Synthetic Chart

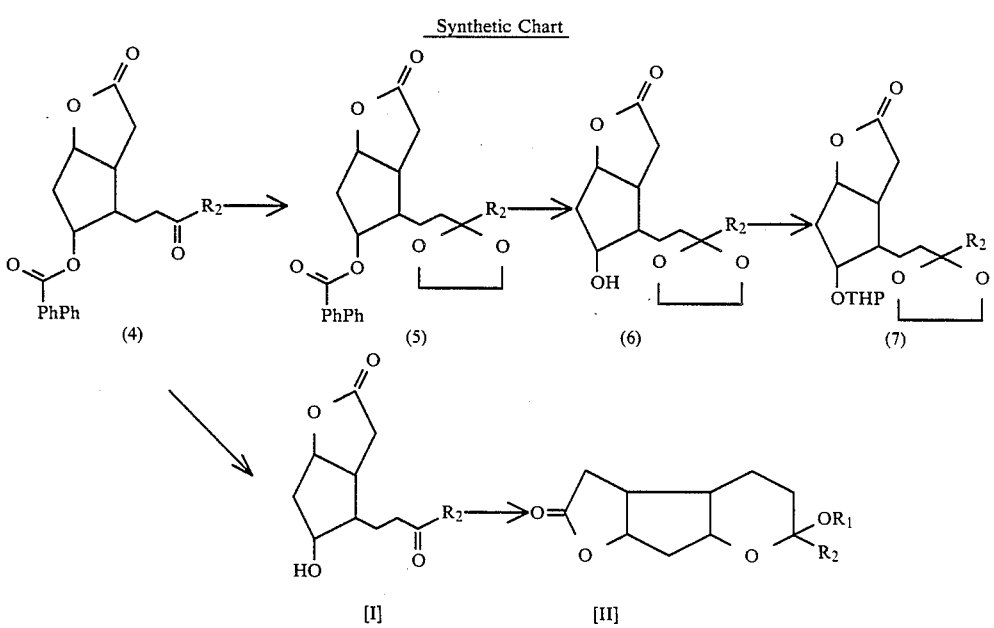

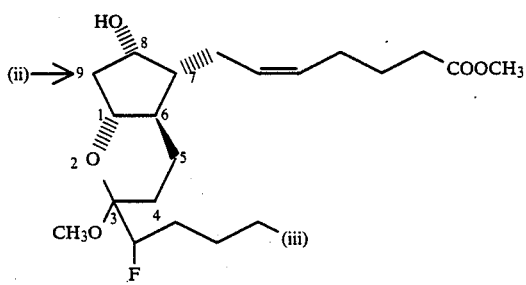

(1R,2R,6S,8R,10RS,10SR)-10-[1(RS)-Fluoropentyl]-10-methoxy-5,9-dioxatricyclo[6.4.0.0$^{2,6}$]dodecane-4-one (1.445 g) was reduced with DIBAL-H (1.5M, 10 ml) in toluene at −78° C. According to a usual work-up a crude lactol was obtained as a diastereoisomer mixture. The obtained material was reacted with an ylide derived from (4-carboxybutyl) triphenylphosphonium bromide in DMSO, and the resultant treated with a usual work-up to give a crude carboxylic acid as a diastereoisomer mixture. The crude carboxylic acid was reacted with a diazomethane solution in ether, and the crude resultant obtained according to a usual work-up was subjected to column chromatography (hexane:ethyl acetate=7: 1-5: 1) to give an isomer having a smaller polarity (0.370 g, 18.5%), an isomer having a larger polarity (0.555 g, 27.8%) of the title compound, and mixture of the both (0.487 g, 24.4%).

The NMR spectrum and the mass spectrum of the isomer having a smaller polarity are:

δ: 0.66-1.04 (3H, m), 1.08-2.63 (23H, m), 3.21(3H, s), 3.06-3.73(1H, m), 3.61(3H, s), 3.94-4.35(1.5H, m), 4.69(0.5H, m), 5.12-5.75(2H, m);

MASS (EI) m/z: 400(M+), 382(M+-H$_2$O), 364(M+-2H$_2$O)

The NMR spectrum and the mass spectrum of the isomer having a larger polarity are:

δ: 0.68-1.04(3H, m), 1.04-2.63(23H, m), 3.17(3H, s), 3.04-3.52(1H, m), 3.63(3H, s), 4.02-4.34(1.5H, m), 4.67(0.5H, m), 5.16-5.64(2H, m).

MASS (EI) m/z: 400(M+), 382M+-H$_2$O), 380(M+-HF).

(3) Synthesis of (1R,3RS,3SR,6R,7R)-7-[6-carbomethoxy-(z)-2-hexenyl]-3-[1(RS)-fluoropentyl]-3-methoxy-2-oxabicyclo[4.3.0]nonane-8-one:

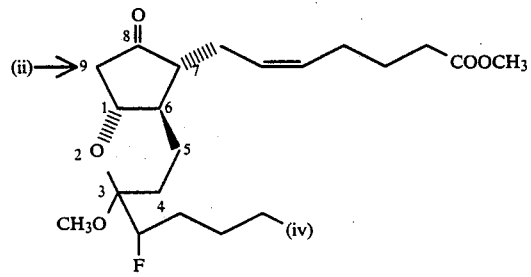

(a) Synthesis of an isomer having a smaller polarity:

An isomer having a smaller polarity of (1R,3RS,3SR,6R,7R,8S)-7-[6-carbomethoxy-(Z)-2-hexenyl]-3-[1(RS)-fluoropentyl]-3-methoxy-2-oxabicyclo[4.3.0]nonane-8-ol (0.233 g) was subjected to Collins oxidation in methylene chloride at room temperature. Into the reaction mixture sodium hydrogen sulfate was added. A crude product obtained by a conventional work-up subjected to column chromatography (hexane:ethyl acetate=4:1) to give an isomer having a smaller polarity of the title compound (0.207 g, 89.7%).

The NMR spectrum and mass spectrum of the obtained compound are:

δ: 0.65-1.06(3H, m), 1.08-2.83(22H, m), 3.29(3H, s), 3.63(3H, s), 3.49-4.00(1H, m), 4.00-4.26(0.5H, m), 4.57-4.80(0.5H, m), 4.86-5.69(2H, m).

MASS (EI) m/z: 398(M+), 380(M+-H$_2$O), 378(M+-HF), 367(M+-OCH$_3$)

(b) Synthesis of an isomer having a larger polarity:

An isomer having a larger polarity of (1R,3RS,3SR,6R,7R,8S)-7-[6-Carbomethoxy-(Z)-2-hexenyl]-3-[1(RS)-fluoropentyl]-3-methoxy-2-oxabicyclo[4.3.0]nonane-8-ol (0.197 g) was subjected to the same manner as described in the above (a) to give an isomer having a larger polarity of the title compound (yield 0.174 g, 88.6%).

The NMR spectrum and mass spectrum of the obtained compound are:

δ: 0.68-1.06(3H, m), 1.06-2.76(22H, m), 3.22(3H, s), 3.63(3H, s), 3.68-4.03(1H, m), 4.06-4.29(0.5H, m), 4.59-4.82(0.5H, m), 5.10-5.56(2H, m).

MASS (EI) m/z: 398(M+), 380(M+-H$_2$O), 378(M+-HF), 367(M+-OCH$_3$).

EXAMPLE 2

(1) Synthesis of (1R,2R,6S,8R,10RS,10SR)-10-ethoxy-10-[1(RS)-fluoropentyl]-10-ethoxy-5,9-dioxatricyclo [6.4.0.0$^{2,6}$]dodecane-4-one:

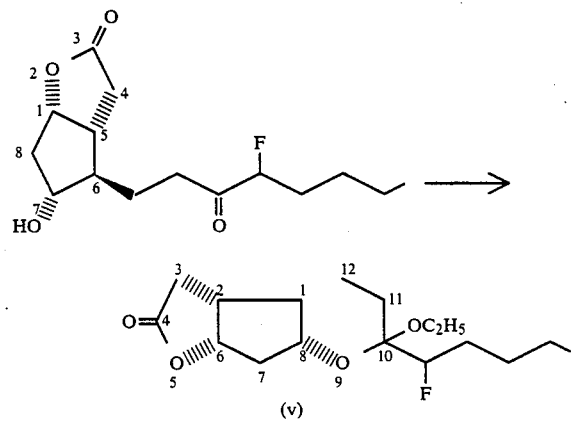

Into a flask equipped with a Soxhlet extractor filled with molecular sieves 3A (1S,5R,6R,7R)-6-[4(RS)-fluoro-3-oxo-1-octyl]-7-hydroxy-2-oxabicyclo[3.3.0]octane-3-one (3.49 g) was charged, and was dissolved in a mixed solvent of ethanol and benzene (1:5), to which a catalytic amount of p-toluene sulfonic acid monohydrate was added, and refluxed for 3 hours. Into the reaction mixture a saturated aqueous solution of sodium bicarbonate was added, and treated by a usual work-up. The obtained crude product was subjected to column chromatography (hexane:ethyl acetate=5:1) to give a diastereoisomer of the title compound (yield: 2.92 g, 67.4%).

The NMR spectrum of the product is:

δ: 0.72-1.02(3H, m), 1.17(3H, t, J=7 Hz), 1.02-2.04(12H, m), 2.04-2.87(4H, m), 3.15-3.82(3H, m), 4.00-4.23(0.5H, m), 4.54-4.97(1.5H, m).

(2) Synthesys of(1R,3RS,3SR,6R,7R,8S)-7-[6-Carboethoxy-(Z)-2-hexenyl]-3-[1(RS)-fluoropentyl]-3-ethoxy-2-oxabicyclo[4.3.0]nonane-8-ol:

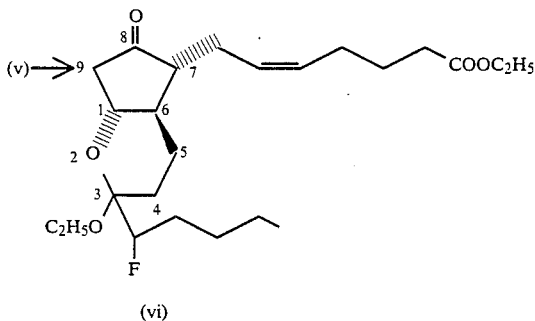

(1R,2R,6S,8R,10RS,10SR)-10-ethoxy-10-[1(RS)-fluoropentyl]-5,9-dioxatricyclo[6.4.0.0²,⁶]dodecane-4-one(2.91 g) was reduced with DIBAL-H (1.5M, 24.6 ml) at −78° C. in toluene. According to a conventional work-up a crude lactol was obtained as a diastereoisomer mixture. The crude product was reacted with an ylide which was obtained from (4-carboxybutyl)triphenylphosphonium bromide in DMSO, and then the product was treated according to a usual work-up to give a crude carboxylic acid as a diastereoisomer mixture. The crude carboxylic acid was dissolved into acetonitrile, to which ethyl iodide (2.96 ml) and DBU (5.54 ml) were added, and stirred at 50° C. for 3 hours. The obtained product was treated with a usual manner, and then subjected column chromatography (hexane:ethyl acetate=5:1) to give an isomer having a smaller polarity 1.232 g (31.0%) and the other isomer having a larger polarity 1.025 g (25.8%) of the titled compound.

NMR spectrum of the both compounds are as follow:
isomer having an smaller polarity:

δ: 0.72–1.04(3H, m), 1.17(3H, t, J=6.5 Hz), 1.23(3H, t, J=6.5 Hz), 1.04–1.90(15H, m), 1.92–2.73(8H, m), 3.15–3.68(3H, m), 4.07(2H, q, J=6.5 Hz), 3.91–4.37(1.5H, m), 4.55–4.75(0.5H, m), 5.15–5.62(2H, m).

isomer having an larger polarity:

δ: 0.73–1.01(3H, m), 1.01–1.88(21H, m), 1.88–2.72(8H, m), 3.09–3.69(3H, m), 4.08(2H, q, J=7 Hz), 3.86–4.37(1.5H, m), 4.56–4.77(0.5H, m), 5.17–5.62(2H, m).

(3) Synthesis of (1R,3RS,3SR,6R,7R)-7-[6-carboethoxy-(Z)-hexenyl]-3-[1(RS)-fluoropentyl]-3-ethoxy-2-oxabicyclo[4.3.0]nonane-8-one:

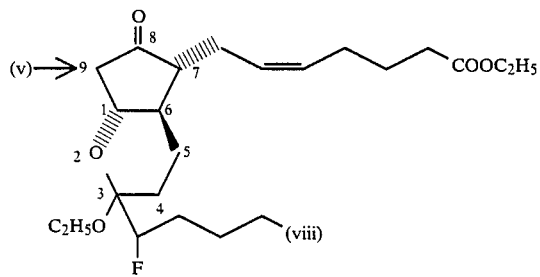

(a) synthesis of an isomer having a smaller polarity:
An isomer having a smaller polarity of (1R,3RS,3SR,6R,7R,8S)-7-[6-carboethoxy-(Z)-2-hexenyl]-3-[1(RS)-fluoropentyl]-3-ethoxy-2-oxabicyclo[4.3.0]nonane-8-ol (0.225 g) was subjected to Collins oxidation at room temperature. Into the reaction mixture sodium hydrogen sulfate was added and treated with a usual work-up. The crude product obtained was subjected to column chromatography (hexane:ethyl acetate=4:1) to give an isomer having a smaller polarity of the title compound (yield 0.180 g, 80.5%). The NMR spectrum of the isomer is as follow:

δ: 0.73–1.05(3H, m), 1.21(3H, t, J=7.5 Hz), 1.23(3H, t, J=7.5 Hz), 1.05–2.80(22H, m), 3.38–3.95(3.5H, m), 4.07(2H, q, J=7.5 Hz), 4.57–4.77(0.5H, m), 5.12–5.68(2H, m)

(b) Synthesis of an isomer having a larger polarity:
According to a manner similar to the just above (a) using an isomer having a larger polarity (0.250 g) instead of the isomer having a smaller polarity the titled compound having a larger polarity was obtained (yield 0.220 g, 88.4%). The NMR spectrum of the isomer is as follow.

δ: 0.72–1.04(3H, m), 1.17(3H, t, J=7.5 Hz), 1.23(3H, t, J=7.5 Hz), 1.04–2.96(22H, m), 3.08–4.24(3.5H, m), 4.07(2H, q, J=7.5 Hz), 4.68–4.87(0.5H, m), 5.08–5.57(2H, m).

(4) Synthesis of (1R,3RS,3SR,6R,7R,8S)-7-(6-carboethoxyhexyl)-3-[1(RS)-fluoropentyl]-3-ethoxy-2-oxabicyclo[4.3.0]nonane-8-ol:

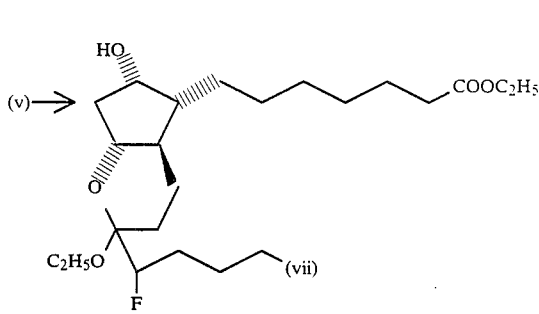

Mixture of a larger polarity isomer and smaller polarity isomer of (1R,3RS,3SR,6R,7R,8S)-3-ethoxy-3-[1(RS)-fluoropentyl]-7-[6-carboethoxy-(Z)-2-hexenyl]-2-oxabicyclo[4.3.0]nonane-8-ol (1.18 g) was dissolved in ethyl acetate, to which 5% palladium/carbon (0.1 g) was added, and the mixture was stirred at 50° C. for 1.5 hours under hydrogen atmosphere. A crude product obtained by treatment of the resultant according to a usual work-up was subjected to column chromatography (hexane:ethyl acetate=5:1) to give the isomer having a smaller polarity (0.177 g, 14.9%), the isomer having a larger polarity (0.329 g, 27.7%) and the mixture thereof (0.558 g, 47.1%). The NMR spectra of the compounds obtained are as follow:.

The NMR spectrum of the isomer having a smaller polarity:

δ: 0.76–1.02(3H, m), 1.02–2.72(31H, m), 2.27(2H, t, J=7.5 Hz), 3.12–3.71(3H, m), 4.08(2H, q, J=7.5 Hz), 3.92–4.48(1.5H, m), 4.52–4.78(0.5H, m).

The NMR spectrum of the isomer having a larger polarity:

δ: 0.74–0.99(3H, m), 0.99–2.80(32H, m), 3.04–3.69(4H, m), 4.07(2H, q, J=7.5 Hz), 3.90–4.38(1.5H, m), 4.57–4.75(0.5H, m).

EXAMPLE 3

Synthesis of [1R,2R,6S,8R,10RS,10SR)-10-heptyl-10-methoxy-5,9-dioxatricyclo[6.4.0.0²,⁶]dodecane-4-one:

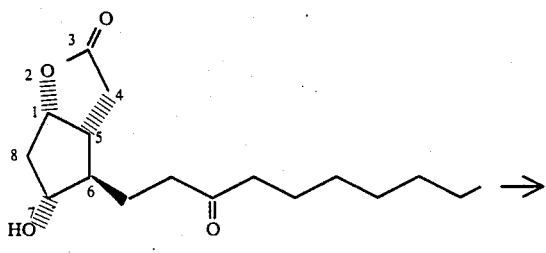

(ix)

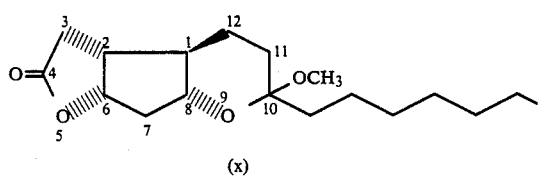

(x)

(1S,5R,6R,7R)-7-hydroxy-6-[3-oxo-1-decyl]-2-oxabicyclo[3.3.0]octane-3-one (0.300 g) was dissolved in methanol, to which p-toluene sulfonic acid monohydrate was added in a catalytic amount, and the mixture stirred at room temperature for 3 hours. To the reaction mixture a saturated sodium bicarbonate solution was added and treated according to a usual work-up. The obtained crude product was subjected to column chromatography (hexane:ethyl acetate=5:1) to give a mixture of diastereoisomer of the title compound (yield 0.274 g, 87.4%). The NMR spectrum of the obtained compound is shown below:

δ: 0.86(3H, t, J=6 Hz), 1.02-2.86(22H, m), 3.11(3H, s), 3.22-3.65(1H, m), 4.63-4.96(1H, m).

EXAMPLE 4

Synthesis of (1R,2R,6S,8R,10RS,10SR)-10-[1(RS)-fluoropentyl]-10-methoxy-5,9-dioxatricyclo [6.4.0.0²,⁶]dodecane-4-one:

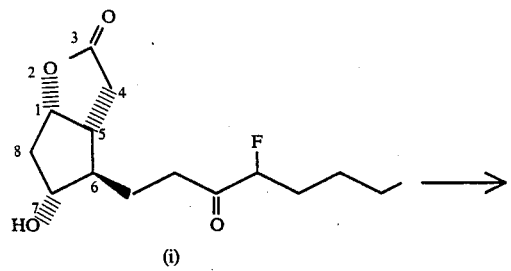

(i)

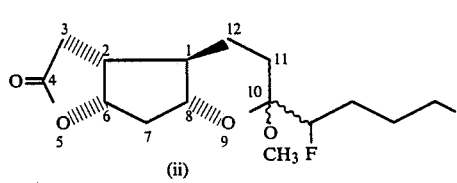

(ii)

To a methanol solution of (1S,5R,6R,7R)-6-[4(RS)-fluoro-3-oxo-1-octyl]-7-hydroxy-2-oxabicyclo[3.3.0]octane-3-one (0.262 g) was added p-toluene sulfonic acid monohydrate (0.018 g). The mixture was refluxed for 5 hr. The mixture was subjected to a similar manner as described in example 1(1) to give the little compound (yields: 0.230 g, 84%).

EXAMPLE 5

Synthesis of (1R,2R, 6S,8R,10RS, 10SR)-10-[1(RS)-fluoro-pentyl]-10-methoxy-5,9-dioxatricyclo[6.4.0.0²,⁶]dodecane-4-one:

According to a similar manner as described in example 4, using (1S,5R,6R,7R)-6-[4(RS)-fluoro-3-oxo-1-octyl]-7-hydroxy-2-oxabicyclo[3.3.0]octane-3-one (0.263 g) and camphor sulfonic acid (0.021 g), the title compound was obtained (yields: 0.236 g, 86%).

EXAMPLE 6

Synthesis of (1R,2R,6S,8R,10RS,10SR)-10-[1(RS)-fluoropentyl]-10-methoxy-5,9-dioxatricyclo[6.4.0.0²,⁶]dodecane-4-one:

To a methanol solution of (1S,5R,6R,7R)-6-[4(RS)-fluoro-3-oxo-1-octyl]-7-hydroxy-2-oxabicyclo[3.3.0]octane-3-one (0.183 g) was added pyridinium p-toluene sulfonate (0.048 g). The mixture was refluxed for 14 hr. The mixture was subjected to the same manner as described in Example 4 to give the title compound (yields: 0.159 g, 83%).

EXAMPLE 7

Synthesis of (1R,2R,6S,8R,10RS,10SR)-10-[1(RS)-fluoro-pentyl]-10-methoxy-5,9-dioxatricyclo[6.4.0.0²,⁶]dodecane-4-one:

To a methanol solution of (1S,5R,6R,7R)-6-[4(RS)-fluoro-3-oxol-octyl]-7-hydroxy-2-oxabicyclo[3.3.0]octane-3-one (0.250 g) was added amberist 15 ® (0.025 g). The mixture was refluxed for 17 hr. The mixture was filtered. The filtrate was concentrated, then subjected to column chromatography (hexane:ethyl acetate=3:2) to give the title compound (yields: 0.150 g, 57%)

What is claimed is:

1. 10-substituted-5,9-dioxatricyclo[6.4.0.0²,⁶]dodecane-4-one represented by following formula [II]:

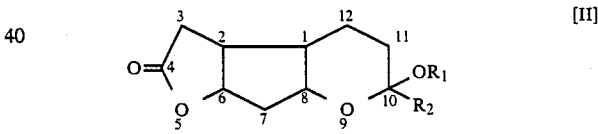

wherein $R_1$ is a hydrocarbon protecting group, and $R_2$ is a saturated or unsaturated hydrocarbon group, which may contain one or more substituent(s) corresponding to the ω-chain of the objective PG's, which may contain one or more substituent(s) selected from the group consisting of halogen, hydroxyl, lower alkyl, alkoxy or phenoxy.

2. A compound of the claim 1, in which the $R_1$ is selected from the group consisting of a $C_1$–$C_9$ alkyl group which may be branched, a $C_5$ or $C_6$ cycloalkyl group, a phenyl group or a benzyl group.

3. A compound of the claim 1, in which the $R_2$ is a saturated or unsaturated $C_1$–$C_9$ alkyl group which may contain one or more substituent(s).

4. A compound of the claim 1 being (1R,2R,6S,8R,10RS,10SR)-10-alkyl-10-alkoxy-5,9-dioxatricyclo[6.4.0.0²,⁶]dodecane-4-one.

5. A compound of the claim 1 being (1R,2R,6S,8R,10RS,10SR)-10-[1(RS)-(substituted)-alkyl]-10-alkoxy-5,9-dioxatricyclo[6.4.0.0²,⁶]dodecane-4-one.

* * * * *